United States Patent [19]

McCombie

[11] 4,314,942
[45] Feb. 9, 1982

[54] DEPROTECTION OF ALLYLIC ESTERS, CARBONATES AND CARBAMATES CATALYZED BY PALLADIUM COMPOUNDS

[75] Inventor: Stuart W. McCombie, West Orange, N.J.

[73] Assignee: Schering Corporation, Kenilworth, N.J.

[21] Appl. No.: 2,472

[22] Filed: Jan. 10, 1979

[51] Int. Cl.$^3$ .................. C07D 501/04; C07D 499/04
[52] U.S. Cl. .................. 260/245.2 R; 260/239 A; 568/830; 568/885; 568/884; 564/458; 260/239.1
[58] Field of Search .................. 260/306.7 C, 239.1, 260/239 A, 245.2 R; 568/830, 885, 884; 564/458

[56] References Cited

PUBLICATIONS

Tetrahedron Letters 43 1970, pp. 3821–3824.
Chemical Communications 21 1970, pp. 1392–1393.
Atkins et al., Tetrahedron Letters 43 pp. 3821–3824, (1970).
Hata et al., Chemical Communications 21 pp. 1392–1393, (1970).
Jac S. 71 725 (1949.
J. Org. Chem. 38 3223 (1973).
Tsuji et al., Tetrahedron Letters 7 613–616 (1979).

*Primary Examiner*—Nicholas S. Rizzo
*Attorney, Agent, or Firm*—Mary S. King; Barbara Renda; Anita W. Magatti

[57] ABSTRACT

An improved synthetic process for the removal of an allyl group in an allylic ester or an allyloxycarbonyl group in an allylic carbonate or carbamate by reaction with 2-ethylhexanoic acid or an alkali metal salt thereof and a catalytic amount of an organic-soluble palladium complex is disclosed herein.

12 Claims, No Drawings

DEPROTECTION OF ALLYLIC ESTERS, CARBONATES AND CARBAMATES CATALYZED BY PALLADIUM COMPOUNDS

BACKGROUND OF THE INVENTION

The N-allyloxycarbonyl group has been used previously as a protecting group for amines and cleaved by hydrogenation after completion of its function. In this respect, the use of allyloxycarbonyl as a protecting group offers no advantages over the more common benzyloxycarbonyl protecting group. See for instance, J. Am. Chem. Soc., 72, 725 (1950). Cleavage of allyloxycarbonyl derivatives of amines and alcohols has also been accomplished using nickel carbonyl as described in *J. Org. Chem.*, 38, 3223 (1973). The disadvantages of this procedure are the necessary basic conditions, as well as a need for an excess of the volatile, toxic nickel carbonyl.

SUMMARY OF THE INVENTION

The present invention describes a new improved synthetic deprotection process for the removal of an allyl group in an allylic ester or an allyloxycarbonyl group in an allylic carbonate or allylic carbamate by reaction of the allylic ester, carbonate or carbamate with 2-ethylhexanoic acid or an alkali metal salt thereof, and a catalytic amount of an organic-soluble palladium complex. The removal of the allyl group or allyloxycarbonyl group of this deprotection procedure provides near-neutral conditions which are particularly desirable for acid- or base-sensitive substrates. Thus, the deprotected acid, alcohol or amine is produced in high yield with a small amount of degradation by-products.

DETAILED DESCRIPTION OF THE INVENTION

The present invention relates to a process for the deprotection of allylic esters, carbonates and carbamates. More particularly, this invention provides a process for the removal of an allyl group in an allylic ester or an allyloxycarbonyl group in an allylic carbonate or which comprises reaction of a solution of the allylic ester, carbonate or carbamate in an organic, non-hydroxylic solvent with 2-ethylhexanoic acid, or an alkali salt thereof, and a catalytic amount of an organic-soluble palladium complex having a coordinating phosphine ligand whereby is produced the free acid, alcohol or amine, respectively.

In the case of the removal of the allyl group from an allylic ester the process most preferably utilizes an alkali metal salt of 2-ethylhexanoic acid. The reaction between the allylic ester and the alkali metal salt of 2-ethylhexanoic acid results in the formation of the alkali metal salt of the product acid which is generally insoluble in the organic, non-hydroxylic solvent utilized for the conduct of the process. As a result of the insolubility of the product salt, the removal reaction is driven to completion by the precipitation of the product salt. This precipitation of the product salt also results in a very pure product without the need for further recrystallizations. The removal of an allyloxycarbonyl group of a carbonate or carbamate to provide the corresponding alcohol or amine is preferably accomplished utilizing the 2-ethylhexanoic acid rather than the alkali metal salt thereof. In this reaction, $CO_2$ is released as a by-product so that the reaction is essentially irreversible.

Suitable allylic protecting groups which are removable by the process of the present invention are any of those present in common allylic alcohols or activated esters thereof which are used to protect the acid, alcohol or amine functionality. Typical allylic alcohols are those such as allyl alcohol, crotyl alcohol and cinnamyl alcohol or the activated esters thereof. For simplicity and economy, allyl alcohol or an activated ester is usually used. Thus, particularly preferred substrates in the practice of this invention are the allylic esters, carbonates and amines wherein the allyl group or allyloxycarbonyl group is derived from allyl alcohol.

2-Ethylhexanoic acid or an alkali metal salt thereof is utilized due to its solubility in most aprotic solvents. Any of the alkali metal salts may be utilized but potassium and sodium are generally preferred.

While 2-ethylhexanoic acid is the acid of choice for use in the present invention, other equivalently functioning carboxylic acids or alkali metal salts thereof may also be utilized provided they do not interfere with other functionalities on the molecule and are suitably soluble in the organic, non-hydroxylic solvent used as the reaction medium.

The reaction proceeds at room temperature generally in a time from about 0.5 to 5 hours. The conditions are generally near neutral so that no other protecting or functional groups are affected during the deprotection procedure. Thus, the invention provides a method of selectively removing an allyl group of an allylic ester or an allyloxycarbonyl group of an allylic carbonate or carbamate while leaving unaffected other protecting groups which might be present in the same molecule. The present invention may also be used to selectively deprotect one of two carboxylic acid functions in a single molecule, for instance, diallyl malonate may be converted to allyl potassium malonate using potassium 2-ethylhexanoic acid.

The solvent utilized for the conduct of this invention may be any common, non-hydroxylic solvent in which the allylic ester, carbonate or carbamate is soluble and in which the 2-ethylhexanoic acid, or the potassium or sodium salt thereof is soluble. Additionally, for ease of isolation, the product acid, (or potassium or sodium salt thereof) should be sparingly soluble or insoluble in the chosen solvent. Suitable solvents include dichloromethane, chloroform, carbon tetrachloride, ethyl ether, benzene, toluene, ethyl acetate, acetone, acetonitrile or a mixture of any of the foregoing.

The organic soluble palladium complex utilized must possess a coordinating phosphine ligand. Preferably triarylphosphine such as the coordinating phosphine ligand. The complex of choice is tetrakis (triphenylphosphine)palladium-(0). Other utilizable soluble palladium complexes are palladium (II), dichloro-di[benzonitrile]palladium (II) and palladium (II) diacetate in conjunction with several equivalents of triphenylphosphine (see Fieser and Fieser, "Reagents for Organic Synthesis", Vol V, pp. 497, 503, 504).

The quantity of catalyst utilized in the process of this invention is typically 0.25–5 mole percent of the allylic ester, carbonate or carbamate substrate, with 2 mole percent being the amount most generally used. However, for large scale preparations, amounts such as 0.25 to 1 mole percent may be sufficient.

In the practice of this invention the acid, alcohol or amine is protected with the allylic group by reaction with a chloride, bromide or iodide of the allylic alcohol or an activated ester thereof in a conventional manner.

Typically, the acid or a salt thereof is reacted with the allyl bromide or iodide in a polar aprotic solvent such as dimethylformamide. The amine or alcohol is typically reacted with the chloroformate or an activated carbonate ester of the allylic alcohol in the presence of an acid acceptor. For instance, 1-aminoadamantane is reacted with allyl chloroformate or with N-[allyloxycarbonyloxy]succinimide.

The present invention is particularly useful for the removal of an allyl group or an allyloxycarbonyl group present in certain acid- or base-sensitive substrates. Particularly preferred substrates are beta-lactam allylic esters such as the allylic esters of penams, e.g., penicillin G, ampicillin; cephems e.g., cephalosporanic acid, 7-(phenylacetamide)desacetoxycephalosporanic acid, cephamycin;carbapenems, e.g., thienamycin and penems. Removal of the allyl group from the foregoing affords useful antibacterial agents of commercial significance. A class of compounds for which this deprotection procedure has been found to be very useful are those of the formula:

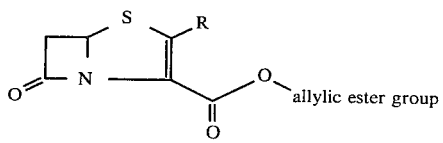

wherein R is hydrogen or lower alkyl of 1–6 carbon atoms. The free acids of these compounds are disclosed in Current Topics in Drug Research, §IV, p. 23–25 (1977). Due to the sensitivity of the penem ring structure to acidic or basic conditions, removal of the conventional protecting groups, e.g., benzyl, benzhydryl, under standard conditions for such protecting groups causes a high percentage of degradation by-products and a low yield of the desired antibacterial 2-alkyl-penem-3-carboxylic acids. See the discussion of Woodward in *Chem. Soc. Special Publications* #28, "Recent Advances in the Chemistry of Beta-Lactam Antibiotics", p. 129 (1976). A further class of penem antibacterial in which the present invention is useful are those described in U.S. Pat. No. 4,070,477 (1978).

Another particularly preferred class of compoounds in the preparation of which the present invention is useful are the 2-(substituted-thio)penem-3-carboxylic acids. (These compounds and methods for their preparation are described in my copending Application U.S. Ser. No. 002,471 entitled "2-(Substituted-Thio)Penem-3-Carboxylic Acids and Congeners" filed concomitantly with this application.

Other carboxylic acids which can be produced from their corresponding allylic esters are those such as amino acids, e.g., glycine, serine, phenylalanine, etc.; benzoic acid and nalidixic acid.

The alcohols and amines which can be produced from their corresponding allylic carbonate or carbamate by the instant process includes alcohols such as n-octadecanol, 1-menthol, 1-oxtanol, 2-octanol, 1-adamantanol, N-benzyloxycarbonylserine; steroids, e.g., cholsterol, cortisone, testosterone, estradiol; phenol, 1-naphthol, macrolides, e.g., erthromycin and rosaramicin; and amines such as 1-aminoadamantane, 2-octylamine, ephedrine, aniline, p-methoxyaniline, 1-naphthylamine, benzocaine, and amino acids, e.g., glycine, phenylalanine and serine.

The following examples describe in detail the process of the present invention and the compounds produced therefrom. It will be apparent to those skilled in the art that many modifications, both of materials and methods, may be practiced without departing from the spirit and scope of the invention.

PREPARATION A

Penicillin-G potassium salt (3.75 g) is stirred in dry dimethylformamide (12 ml) with addition of allyl iodide (1.65 g) at room temperature for 18 hours. The mixture is then diluted with ether (100 ml), and washed with water (3×50 ml), 5% aqueous sodium thiosulfate (25 ml) and saturated sodium chloride (50 ml). After drying over anhydrous magnesium sulfate, the solvents are removed and the residue dried to constant weight under high vacuum to give penicillin-G allylester in near-quantitative yield, as a colorless oil with an IR spectrum in dichloromethane solution at 3350, 1785, 1730 and 1660 cm$^{-1}$.

PREPARATION B

The procedure of Preparation A is repeated with the allyl iodide being replaced by cinnamyl bromide (1.95 g). The penicillin-G cinnamyl ester is isolated in the same manner, as a white foam, with an IR spectrum in dichloromethane at 3300, 1785, 1670 and 1610 cm$^{-1}$.

PREPARATION C

The procedure of Preparation A is followed using redistilled methyl gamma-bromocrotonate (1.75 g) in place of the allyl iodide. The product, penicillin-G 3-(methoxycarbonyl)allyl ester is isolated in the same manner as a colorless, thick oil with an IR spectrum in dichloromethane at 3350, 1785, 1735, 1715 and 1680 cm$^{-1}$.

PREPARATION D

Penicillin-G allyl ester (10 mmol; 3.75 g) is treated at 0°–50° C. in dichloromethane (20 ml) with m-chloroperoxybenzoic acid (10.2 mmol; 1.75 g) in ethyl ether (5 ml). The solution is kept at 0°–5° C. for two hours, then diluted with dichloromethane (30 ml) and washed 2×50 ml sodium bicarbonate solution, dried and evaporated to afford a residue (foam) of the sulfoxide of penicillin-G allylester. This foam is dissolved in dry dioxane (50 ml) and refluxed for 10 hours with pyridine phosphate (0.2 g). The solvent is evaporated and the residue chromatographed on silica gel, eluting with 5% ether-dichloromethane. Evaporation of appropriate eluates gives allyl-7-phenylacetamidoesacetoxycephalosporanate, as a white foam, with an IR spectrum in dichloromethane with $v_{max}$ at 3400, 1770, 1725, 165 and 1605 cm$^{-1}$.

PREPARATION E

4-Acetylthioazetidin-2-one (Annalen, 1974, p. 553) (1.4 g) and allyl glyoxylate hydrate (1.5 g) are refluxed for 2 hours in benzene to afford a solution of 1-(allyloxycarbonylhydroxymethyl)-4-acetylthioazetidin-2-one which is cooled and used directly in the next step.

The foregoing solution is diluted with dichloromethane (30 ml) and methanesulfonyl chloride (1.5 ml), and triethylamine (2.3 ml) is added over 2 minutes with stirring. After 5 minutes, the solution is washed with 0.2N sulfuric acid and then with water. After drying over anhydrous magnesium sulfate and evaporation, the crude 1-(allyloxycarbonylchloromethyl)-4-acetylthioazetidin-2-one is isolated as a brown oil.

The crude chloride from the previous paragraph is stirred in dry dichloromethane (15 ml) and dry dimethylformamide (15 ml) with triphenylphosphine (3.25 g) and 2,4,6-collidine (1.5 g) for 20 hours. The reaction mixture is diluted with dichloromethane and washed with 3×50 ml water, dried and evaporated. The residue is dried at high vacuum, then chromatographed on silica gel (100 g), eluting with dichloromethane followed by 25% ether:dichloromethane. Fractions containing a mixture of the phosphorane and triphenylphosphine oxide are combined and evaporated.

The phosphorane prepared in the previous paragraph is heated at reflux for 1.5 hour in toluene (50 ml). After being cooled and evaporated, the residue is chromatographed on silica gel, eluting with 2:1 dichloromethane:hexane, followed by dichloromethane. Fractions containing the product are evaporated to give a pale yellow oil, which is crystallized on strong cooling to give allyl 2-methylpenem-3-carboxylate. Infrared spectrum in dichloromethane: 1795, 1965, 1640 cm$^{-1}$.

PREPARATION F

1-Aminoadamantane (10 mmol; 1.51 g) and triethylamine (1.9 ml) in dry dichloromethane (30 ml) are stirred at 0°–5° C. and allyl chloroformate (1.1 ml) added dropwise. After 0.5 hour, the solution is washed with dilute sulfuric acid and water. After drying over anhydrous magnesium sulfate, the solution is evaporated to give 1-(allyloxycarbonylamino)adamantane, as a white solid, with a melting point of about 56°–58° C.

EXAMPLE 1

Pencillin-G allylester (0.38 g) is stirred under argon in a 0.5M dichloromethane solution of potassium 2-ethylhexanoate (3 ml) and ethyl ether (2 ml). Triphenylphosphine (0.025 g) and tetrakis (triphenylphosphone)palladium-(0) (0.020 g) are added, and stirring continued for 1 hour at room temperaure. Ethyl ether (10 ml) is added and the product filtered, washed with 1:1 ether:-dichloromethane and dried in vacuo at 50° C. to give pure potassium penicillin-G (0.34 g), identical (IR, p.m.r.) with an authentic sample in a yield of about 90%.

EXAMPLE 2

When the tetrakis (triphenylphosphine)palladium-(0) in Example 2 is replaced by bis (triphenylphosphine)-palladium (II)dichloride (0.015 g), pure potassium penicillin-G is obtained.

EXAMPLE 3

Penicillin-G cinnamyl ester (0.50 g) is stirred in ethyl ether (5 ml) and a 0.5M solution of potassium 2-ethylhexanoate (3.5 ml) in dichloromethane added. Then triphenylphosphine (0.025 g) and tetrakis (triphenylphosphine)palladium-(0) (0.22 g) are added, and the mixture is stirred for 1 hour under argon. After dilution with ethyl ether (10 ml), the precipitate is filtered and dried to afford pure potassium penicillin-G in a yield of about 85%.

EXAMPLE 4

The procedure of Example 3 is repeated with the penicillin-G cinnamyl ester being replaced by penicillin-G-(3-methoxycarbonylallyl)ester (0.46 g) to afford pure potassium penicillin G in a yield of 79%.

EXAMPLE 5

Allyl 2-methylpenem-3-carboxylate (0.10 g) is stirred in ethyl ether (1.5 ml) with a 0.5M dichloromethane solution of potassium 2-ethylhexanoate (1.25 ml). Triphenylphosphine (0.01 g) and tetrakis (triphenylphosphine)palladium-(0) (0.01 g) are added, and the mixture stirred under argon for 45 minutes at room temperature. After dilution with ethyl ether (3 ml), the product is collected, washed with ethyl ether and dried in vacuo at room temperature to give, as a cream solid, potassium 2-methylpenem-3-carboxylate having infrared $v_{max}$ (nujol) at 1785 and 1605 cm$^{-1}$ in a yield of about 86%.

EXAMPLE 6

Allyl 7-(phenylacetamido)-desacetoxycephalosporanate (1.0 g) is stirred with potassium 2-ethylhexanoate in dichloromethane (0.2M; 12 ml), triphenylphosphine (0.08 g) and bis(triphenylphosphine)palladium dichloride (0.03 g) for 1.5 hours under argon. The product is collected and washed with dichloromethane. After drying at 50° C. in vacuo, there is afforded potassium 7-(phenylacetamido)desacetoxycephalosporanate, identical with an authentic sample.

EXAMPLE 7

1-(Allyloxycarbonylamino)adamantane (0.50 g) is stirred in dichloromethane (10 ml) containing 2-ethylhexanoic acid (0.35 g). Triphenylphosphine (0.05 g) and tetrakis-(triphenylphosphine)palladium (0.04 g) are added and the mixture is stirred at room temperature for 1 hour. Ethyl ether (10 ml) is added, and the product collected, washed with ether, and dried at 25° C. in vacuo, which is identical (IR, mp and pmr) with an authentic sample of 1-aminoadamantane prepared from the acid and amine in ether.

EXAMPLE 8 n-Octadecyl allyl carbonate (0.5 g) [prepared as described in J. Org. Chem., 38, 3223 (1973)] and ethylhexanoic acid (0.2 g) are stirred for 1 hour under nitrogen in dichloromethane (5 ml) containing triphenylphosphine (0.025 g) and tetrakis (triphenylphosphine)palladium-(0) (0.02 g). Thin layer chromatography indicates complete conversion to products after addition is complete. The mixture is diluted with ethyl ether, washed with sodium bicarbonate, dried and evaporated. The residue is chromatographed on silica gel and eluted with 1:1 dichloromethane:hexane in order to remove the allyl 2-ethylhexanoate, and with 5% ether-dichloromethane in order to elute the product, n-octadecanol, fully identical with an authentic sample.

EXAMPLE 9

Allyl l-menthyl carbonate (0.3 g) [prepared as described in J. Org. Chem., 38, (1973)] is substituted for the n-octadecyl derivative of Example 8. Cleavage is completed within 1 hour, and the product, l-menthol, is isolated by chromatography.

What is claimed is:

1. A process for the removal of an allyl group in an allylic ester formed from a carboxylic acid and an allylic alcohol or derivative thereof or an allyloxycarbonyl group in an allylic carbonate or allylic carbamate formed from an alcohol or amine and an allylic alcohol chloroformate or allylic alcohol activated ester, which comprises:

reaction of a solution of the allylic ester, carbonate or carbamate in an organic, non-hydroxylic solvent with 2-ethylhexanoic acid, or an alkali metal salt thereof, and a catalytic amount of an organic-soluble palladium complex having a corrdinating phosphine ligand, said catalytic amount of palladium complex being from about 0.25 to about 5 molar percent of said allylic ester, cabonate or carbamate, respectively.

2. The process according to claim 1 wherein the coordinating phosphine ligand of the soluble palladium complex is triphenylphosphine.

3. The process according to claim 2 wherein soluble palladium complex is tetrakis (triphenylphosphine)palladium-(0).

4. The process according to claim 1 wherein the amount of soluble palladium complex is 2 mole percent.

5. The process according to claim 1 wherein the process involves the removal of an allyl group in an allylic ester formed from a carboxylic acid and an allylic alcohol or derivative thereof and utilizes an alkali metal salt of 2-ethylhexanoic acid.

6. The process according to claim 5 wherein the alkali metal salt of 2-ethylhexanoic acid is a potassium or sodium salt.

7. The process according to claim 5 wherein the allylic ester is a beta-lactam allylic ester formed from the carboxylic acid of the beta-lactam and an allylic alcohol or derivative thereof.

8. The process according to claim 7 wherein the beta-lactam allylic ester is a penam allylic ester formed from the carboxylic acid of the penem and an allylic alcohol or derivative thereof.

9. The process according to claim 7 wherein the beta-lactam allylic ester is a cephalosporin allylic ester formed from the carboxylic acid group of the cephalosporin and an allylic alcohol or derivative thereof.

10. The process according to claim 7 wherein the beta-lactam allylic is a carbapenem allylic ester formed from the carboxylic acid of the carbapenem and an allylic alcohol or derivative thereof.

11. The process according to claim 7 wherein the beta-lactam allylic ester is a penem allylic ester formed from the carboxylic acid of the penem and an allylic alcohol or derivative thereof.

12. The process according to claim 11 wherein the penem allylic ester is of the formula

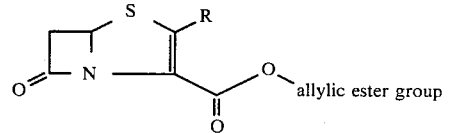

wherein R is hydrogen or lower alkyl of 1–6 carbon atoms.

* * * * *